(12) United States Patent
Rowe

(10) Patent No.: US 6,406,451 B1
(45) Date of Patent: Jun. 18, 2002

(54) DRY HANDLE SWAB ASSEMBLY

(75) Inventor: John Rowe, Antioch, IL (US)

(73) Assignee: Zila, Inc., Phoenix, AZ (US)

( * ) Notice: Subject to any disclaimer, the term of this patent is extended or adjusted under 35 U.S.C. 154(b) by 0 days.

(21) Appl. No.: 09/866,302

(22) Filed: May 24, 2001

(51) Int. Cl.$^7$ ............................................. A61M 35/00

(52) U.S. Cl. ........................................................ 604/1

(58) Field of Search ........................................ 604/1–3

(56) References Cited

U.S. PATENT DOCUMENTS

| 3,163,160 | A | * | 12/1964 | Cohen | |
| 4,211,323 | A | * | 7/1980 | Olsen | 206/210 |
| 4,952,204 | A | * | 8/1990 | Korteweg | 604/1 |
| 6,039,487 | A | * | 3/2000 | Kristiansen | 401/126 |

FOREIGN PATENT DOCUMENTS

EP 0357261 * 3/1990 ............. 604/1

* cited by examiner

Primary Examiner—Dennis Ruhl
(74) Attorney, Agent, or Firm—Drummond & Duckworth

(57) ABSTRACT

An improved swab applicator is provided including a swab connected to an elongate stick. The swab applicator further includes a sleeve encapsulating the swab and stick including a handle portion, receptacle portion and transition portion. The handle portion is preferably hollow and cylindrical in shape extending a substantial part around the length of the stick, while the receptacle portion of the sleeve is also hollow and cylindrically shaped having a substantially greater cross section than the handle portion. Meanwhile, the transition portion is preferably hollow and fristo conically shaped to connect the handle portion to the receptacle portion of the sleeve. The transition portion is substantially non-deformable when the receptacle portion of the sleeve is compressed creating a significant level of sheer stress to be imparted between the receptacle portion and transition portion of the sleeve causing the receptacle portion to sever from the rest of the sleeve.

8 Claims, 3 Drawing Sheets

DRY HANDLE SWAB ASSEMBLY

BACKGROUND OF THE INVENTION

The present invention relates to swab applicators for applying various liquids such as cleansers, antiseptics, medicaments and cosmetics. More particularly, the present invention relates to single use prepackaged swab applicators.

A self-contained disposable swab is a useful device for applying liquid solutions to objects, particularly for applying topical solutions such as cleansers, antiseptics, medicaments and cosmetics to the human body. Prior to the development of such self-contained applicators, the various solutions were stored in capped bottles containing much more solution than would be applied during a single use. Dry absorbent swabs, such as the common cotton swab were stored in a separate container. The cotton swabs often included a wood stick attached to the swab. A user, would place the cotton swab within the capped bottle so that the solution would be absorbed into the swab. The solution would then be applied to an object in typical manner.

There were several inconveniences and disadvantages associated with this system. For example, it would be inconvenient for persons such as doctors or dentists to store relatively large bottles of various solutions. In addition, dipping the absorbent swabs within bottles could be messy and time consuming. Moreover, where the dipped swab had been placed in contact with contaminants, the swab could not be re-dipped into the bottle to absorb more solution. Instead, a new swab applicator had to be used for each application.

Self-contained swab applicators have proven to be a convenient solution to overcoming these problems. Each applicator stores a preselected amount of solution determined to be appropriate for one usage. The solution is sealed when not in use so that the applicator may be stored and carried in a doctor's office or doctor's bag until the applicator is needed. A swab in a closed container is disclosed in U.S. Pat. No. 2,902,146 issued Sep. 1, 1999 which describes a sterile package in which a surgical swab is sealed within a casing. U.S. Pat. No. 3,776,220 issued Dec. 4, 1973 describes an applicator in which a diagnostic swab and culture medium are contained within different sections of the same plastic tube with the two sections being separated by a frangible seal. Meanwhile, numerous U.S. patents describe applicators having an absorbent swab associated with a sealed reservoir storing a liquid. The reservoirs are typically fractured to release the liquids to the absorbent swab. Unfortunately, these reservoirs can sometimes be difficult to rupture. Moreover, several of these applicators require that glass or plastic shards be maintained within the swab when the swab is used to topically apply a liquid to a person.

An attempt to overcome several of these disadvantages is described in U.S. Pat. No. 4,952,204 issued on Aug. 28, 1990 to Korteweg. This reference describes a swab applicator in which a swab is attached to a plastic stick. The applicator further includes a sleeve containing a medicinal, cleaning or cosmetic liquid which encapsulates the swab and engages the stick. The sleeve is compressed at a particular location causing it to sever from the swab applicator. Unfortunately, it has been found that it takes significant manual force and/or repeated compression upon the sleeve to sever the sleeve from the rest of the swab applicator.

Despite the significant level of activity in the art directed to developing a prepackaged swab applicator, there exists a need for an improved prepackaged swab applicator which is capable of being easily opened by the consumer, while still providing a sturdy package able to withstand the rigors of distribution and handling. In addition, it would be desirable to provide a prepackaged swab applicator that can be used and disposed of easily and conveniently. Moreover, it would be desirable to provide a prepackaged swab applicator which is inexpensive to manufacture and provides significant flexibility so that various types of consumer products can be dispensed into and by the swab applicator.

SUMMARY OF THE INVENTION

The present invention addresses the aforementioned disadvantages by providing an improved prepackaged swab applicator. The prepackaged swab applicator is sealed and openable, and includes a swab attached to the end of an elongate small diameter stick. The swab applicator further includes a thin walled hollow sleeve which encompasses the swab and stick. Preferably, the sleeve is constructed of a single piece of rigid plastic material that is manually compressible and separable at defined regions.

The swab applicator sleeve is divided into three sections, including a handle portion, a receptacle portion and a transition portion. The handle portion encompasses and attaches to the free end of the stick by frictional engagement, or adhesive or other means known to those skilled in the art. The cross section of the receptacle portion is substantially larger than that of the handle portion of the sleeve and sized to encapsulate the swab. Preferably, the receptacle portion of the sleeve is cylindrical and has a diameter of approximately three times that of the handle portion.

Meanwhile, the transition portion of the sleeve is tapered and connects the handle portion of the sleeve to the receptacle portion of the sleeve. In contrast to prior art sleeved swab applicators, the transition portion of the sleeve is constructed to not significantly deform when the receptacle portion of the sleeve is compressed. In a preferred embodiment, the transition portion projects outwardly at an angle greater or equal to 45° from the axis of the swabstick immediately adjacent to where the transition portion engages the receptacle portion of the sleeve. It has been discovered that increasing the angle at which the transition engages the receptacle portion, decreases the transition portion's propensity to compress when the receptacle portion of the sleeve is manually compressed. Moreover, the increased angle at which the transition portion projects outwardly causes a stress razor to be formed where the transition portion engages the receptacle portion of the sleeve. This stress razor undergoes significant sheer stress when the receptacle portion of the sleeve is compressed. The sleeve is constructed to include a sufficiently thin wall thickness at the stress razor so that the sleeve ruptures due to the sheer stresses caused by manual compression of the receptacle portion of the sleeve.

The swab applicator may be constructed of various sizes and configurations depending on the intended purpose of the swab applicator. However, in a preferred embodiment for applying medicinal, cleansing and cosmetic liquids, the swab applicator includes a swab stick approximately 8 centimeters long and 2.5 millimeters in diameter, and has a swab at the stick's distal end that is approximately 17 millimeters in length and 5 millimeters in diameter. For this preferred embodiment, the sleeve is approximately 7.5 millimeters in diameter, 10 centimeters long and includes a stick portion 3 centimeters in length, a transition portion 0.5 centimeters in length and a receptacle portion 6.5 centimeters in length. The stick and sleeve are preferably constructed of plastic materials, while the swab is preferably constructed of a cotton or nylon material. Of course, changes in the materials or construction of the swab applicator of the present invention may be made without departing from the spirit and scope of the invention.

The swab applicator of the present invention is thus capable of being easily opened by the consumer while being simple and inexpensive to manufacture. The swab applicator is also neat and convenient to handle without the consumer soiling his or her hands or the surrounding area.

DETAILED DESCRIPTION OF THE INVENTION

Figure 1:
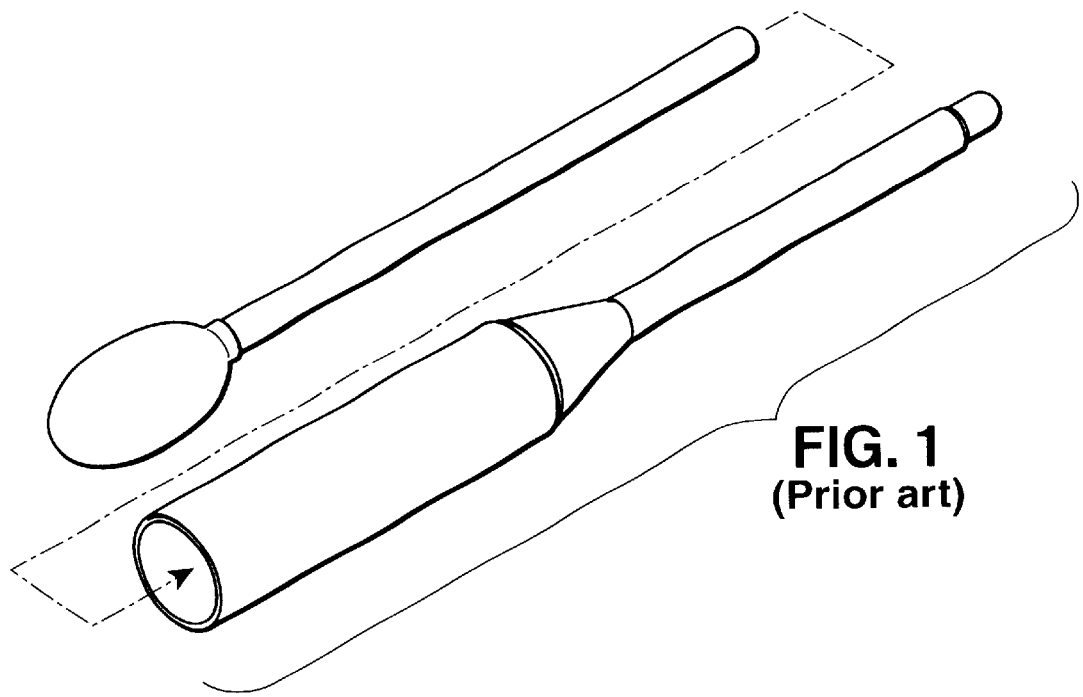
FIG. 1 is a perspective view of a swab applicator of the prior art.
Figure 2:
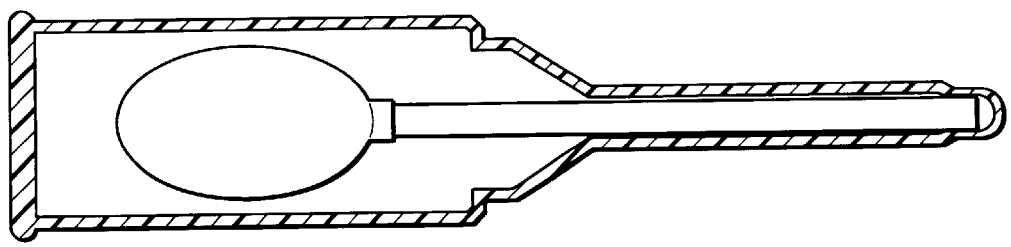
FIG. 2 is a cross sectional view of the swab applicator of the prior art shown in FIG. 1.
Figure 5:
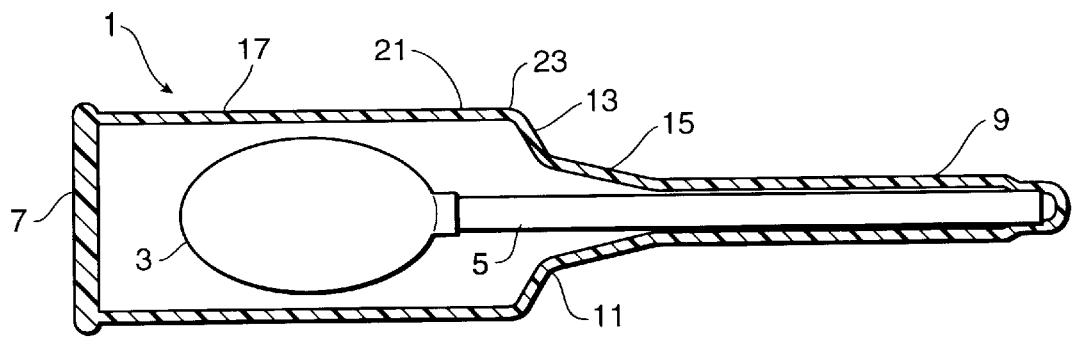
FIG. 5 is a cross sectional view of the swab applicator of the present invention.

While the present invention is susceptible of embodiment in various forms, as shown in the drawings, hereinafter will be described the presently preferred embodiments of the invention with the understanding that the present disclosure is to be considered as an exemplification of the invention, and it is not intended to limit the invention to the specific embodiments illustrated.

With reference to FIGS. 5–9, the swab applicator 1 of the present invention includes a swab 3 constructed of an absorbent material such as cotton for absorbing a cleanser, medicament or cosmetic. Attached to the swab 3 is a thin elongate stick 5 constructed of various materials such as wood or plastic. The longitudinal axis of the stick defines a stick axis. The swab applicator 1 of the present invention further includes a sleeve 7. The sleeve 7 is preferably circular in cross section, hollow along its entire length, and fabricated from a plastic material.

Figure 6:
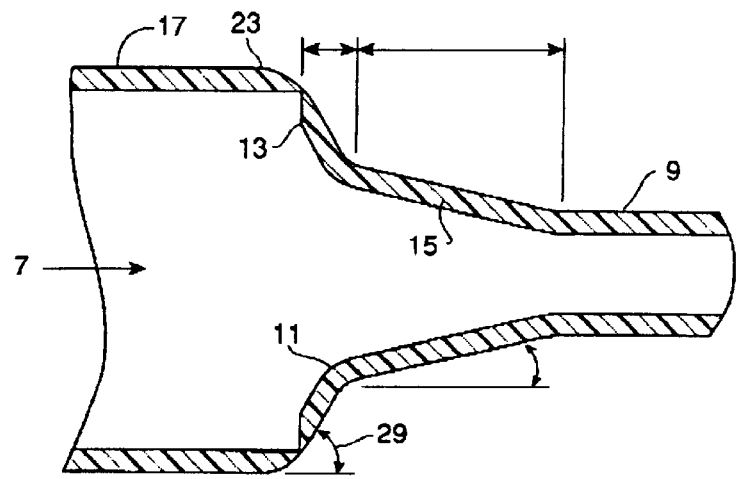
FIG. 6 is a partial cross sectional view illustrating the receptacle portion, transition portion and handle portion of the sleeve of the swab applicator of the present invention.

The sleeve 7 is constructed to encapsulate the swab 3 and stick 5, and constructed in three definite portions including a handle portion 9, transition portion 11 and receptacle portion 17. The handle portion 9 has a relatively small diameter cylindrical construction which at least partially frictionally engages the stick 5 along its length. At the opposite extremity of the stick and sleeve is the hollow cylindrically shaped receptacle portion 17 which has a relatively large diameter for receiving the swab 3 within the receptacle portion's hollow center. Connecting the handle portion 9 to the receptacle portion 17 is hollow substantially fristoconically shaped transition portion 11. With reference particularly to FIG. 6, the transition portion 11 is annularly positioned relative to the stick 5 and stick axis. In addition, the transition portion 11 has a relatively small diameter where it engages the handle portion 9 of the sleeve but projects outwardly along its length until engaging the receptacle portion 17. The sleeve 7 further includes a compression region 21 and severance region 23. The compression region 21 is that location on the receptacle portion 17 of the sleeve adjacent to the transition portion 11 of the sleeve wherein compression causes the receptacle portion to sever at the severance region 23 from the transition portion. Of importance, for purposes of the present invention, the transition portion is constructed so as not to significantly compress when the compression region of the receptacle portion is manually compressed.

With reference to FIGS. 1–4, the prior art includes a swab applicator including a swab, stick and sleeve. The sleeve includes a handle portion, transition portion and receptacle portion, and a liquid solution positioned within the receptacle portion of the sleeve to be absorbed by the swab. This swab applicator of the prior art is described in U.S. Pat. No. 4, 952,204 which is incorporated by reference herein.

Figure 3:
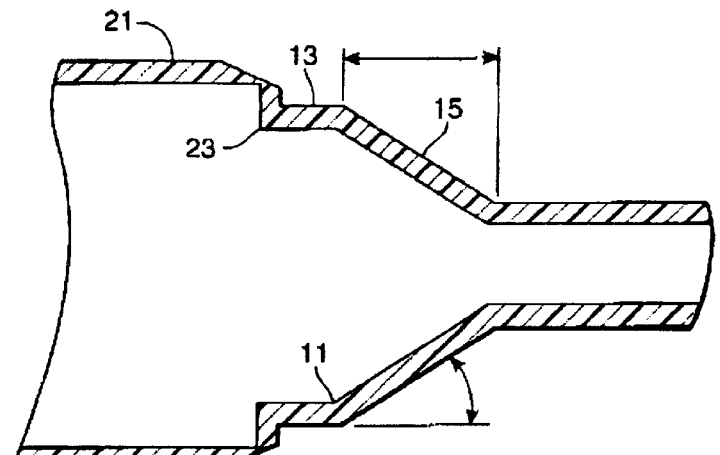
FIG. 3 is a partial cross sectional view illustrating the receptacle portion, transition portion and handle portion of the sleeve of a swab applicator of the prior art.
Figure 4:
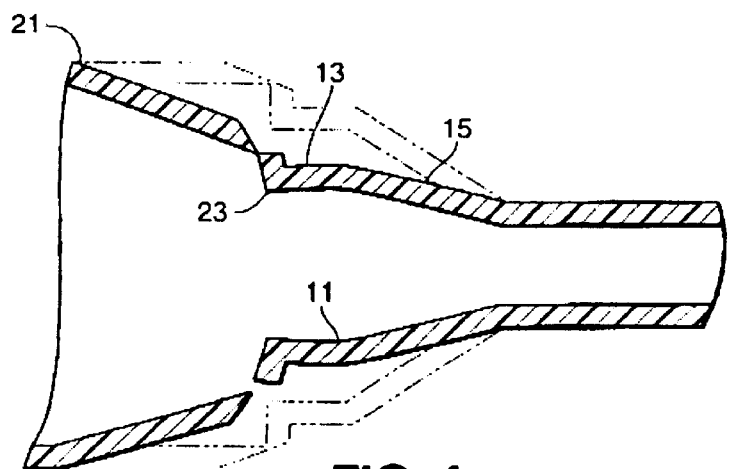
FIG. 4 is a partial cross sectional view illustrating compression of the receptacle portion of the sleeve adjacent to the transition portion of the sleeve.

To remove the receptacle portion of the sleeve, as shown in FIG. 4, the receptacle portion is manually compressed by one's fingers causing the receptacle portion and transition portion to be forced inwardly causing the severance region of the sleeve to flatten. This flattening of the sleeve creates a bending moment to be introduced into the sleeve, particularly where the receptacle portion intersects with the transition portion of the sleeve. This bending moment causes the interior 33 of the sleeve to be placed in tension, and the exterior 35 of the sleeve to be placed in compression, particularly at the severance point 23. The compression and tensional stresses causes the severance region to tear or crack, particularly after repeated compression and decompression of the receptacle portion of the sleeve which induces a fatigued failure at the severance region. Unfortunately, it can be difficult to sever the receptacle portion from the prior art swab applicator illustrated in FIGS. 1–4 as it takes significant manual force and/for repeated compression and decompression upon the sleeve to sever the receptacle portion from the rest of the swab applicator.

Figure 7:
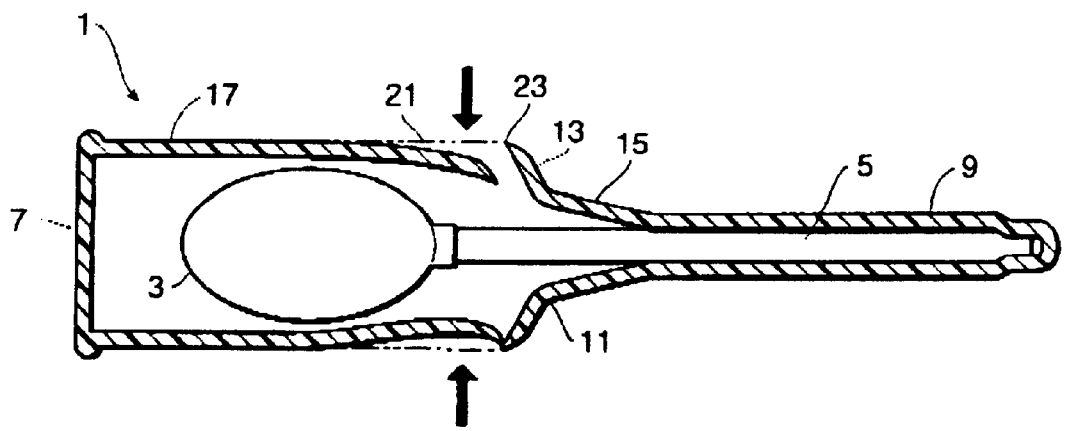
FIG. 7 is a cross sectional view of the swab applicator of the present invention illustrating compression of the receptacle portion of the sleeve adjacent to the transition portion of the sleeve.

With reference to FIGS. 5–9, the swab applicator 1 of the present invention overcomes this disadvantage by including a transition portion of the sleeve which does not significantly compress when the receptacle portion of the sleeve is compressed. As illustrated in FIG. 7, when the receptacle portion's compression region 21 is compressed, the transition portion 11 is constructed to maintain its shape and not deform, particularly immediately adjacent to where the transition portion engages the receptacle portion of the sleeve. Though a significant bending moment, induced by compression of the compression region, is imparted upon the severance region 23 of the sleeve 7, as would be understood by those skilled in the art, a significant additional sheer stress is also imparted upon the severance region making it significantly easier for persons to sever the receptacle portion 17 from the rest of the sleeve.

The sleeve 7 may be manufactured in various different constructions so that the transition portion does not compress or deform when the receptacle portion is compressed. For example, though not shown in the figures, the transition portion may be constructed with a significantly greater thickness than the receptacle portion of the sleeve. The thicker material will impede compression of the transition portion. In the alternative, the transition portion 11 may be constructed of a harder or stronger material than the receptacle portion to impede compression or deformation of the transition portion. However, in a preferred embodiment, the swab applicator 1 of the present invention is constructed with the transition portion projecting outward from the stick axis at an angle of greater than or equal to 45° where the transition portion engages the receptacle portion of the sleeve, referred to herein as an engagement section.

With reference to FIG. 3 and as shown and described in U.S. Pat. No. 4,952,204, a first prior art swab stick included a transition portion having a cylindrical element 13 and a fristoconical element 15. The cylindrical section 13 is immediately adjacent to the receptacle section of the sleeve and engages the receptacle portion at an angle of 0° relative to the stick axis. Meanwhile, the fristoconical section projects away from the stick axis at an angle of approximately 30°. In an alternative prior art embodiment, and as shown in FIG. 6 of U.S. Pat. No. 4,952,204, the transition portion of the sleeve is constructed of a single fristoconically shaped element which includes an angled sidewall extending from the handle portion to the receptacle portion of the sleeve at an angle of approximately 30° relative to the stick axis. Still an additional prior art swab applicator sold commercially under the name Zilactin® toothache swab includes a transition portion having a substantially fristoconically shaped section angled at approximately 41° relative to the stick axis where the transition portion engages the receptacle portion of the sleeve. When each of the receptacle portions of the prior art swab applicators are compressed, the transition portion of the sleeve also compresses and deforms impeding the creation of any significant sheer stresses in the severance region of the sleeve.

Figure 8:
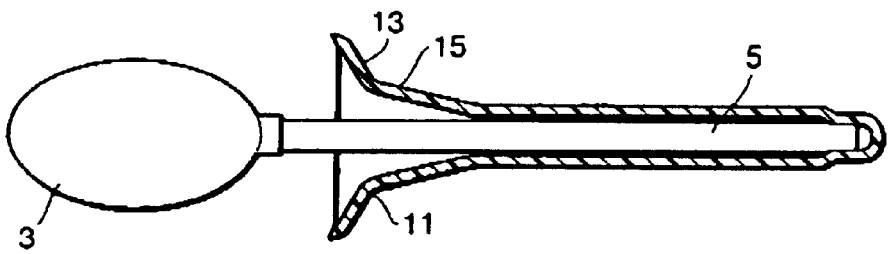
FIG. 8 is a cross sectional view of the swab applicator of the present invention with the receptacle portion of the sleeve severed from the transition portion of the sleeve.
Figure 9:
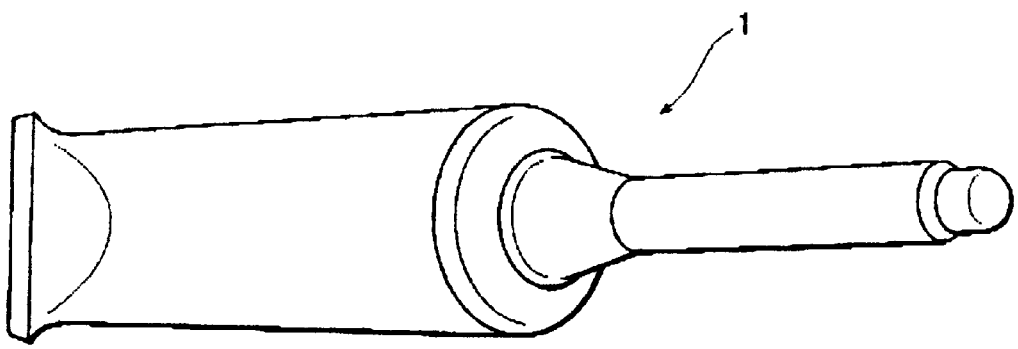
FIG. 9 is a perspective view of the swab applicator of the present invention.

With reference to FIGS. 7 and 8, the preferred swab applicator 1 includes a transition portion constructed of a first hollow fristoconically shaped section 13 and a second fristoconically shaped section 15. The first section 13 extends outwardly at an angle 29 greater than or equal to 45°. In a preferred embodiment, the transition portion engages the receptacle portion of the sleeve at an angle of approximately 49° relative to the stick axis. This angle of 49° has been found to be sufficiently great to impede compression and deformation of the transition portion where the receptacle portion of the sleeve is compressed, but not so great as to impede compression of the receptacle portion of the sleeve at the compression region 21. Moreover, since the cylindrical sidewall of the receptacle portion of the sleeve is parallel to the stick axis, the transition portion engages the receptacle portion at an angle of 49°. This angle has been found to provide a sufficient stress razor to provide adequate separation of the receptacle portion to the transition portion of the sleeve when compressed. The severance region may also be notched to provide further assistance to sever the receptacle portion from the transition portion of the sleeve.

Thus, it can be seen that the present invention provides an improved swab applicator including a swab, stick, sleeve and solution contained within the sleeve. The sleeve provides an enclosure which is secure, but nonetheless readily openable by manual force. The transition portion of the sleeve also provides an integral element for shielding the user's hand from liquid absorbed by the swab.

Having described my invention in such terms to enable those skilled in the art to make and use it, and having identified the present and preferred embodiment thereof, I claim:

1. A sealed openable swap applicator comprising:
a swab;
an elongate small diameter stick attached to said swab, said stick defining a stick axis;
a thin walled sleeve assembly for encapsulating said swab and stick constructed of a relatively rigid plastic material that is manually compressible and severable at a desired region, said sleeve assembly including a handle portion, a receptacle portion and a transition portion therebetween;
said handle portion engaging said stick, and extending and encompassing a substantial part of the length of said stick;
said receptacle portion substantially enveloping said swab and being of a substantially greater cross section than said handle portion, said receptacle portion also including a compression region adjacent to said transition portion wherein compression of said compression region causes said receptacle portion to sever from said transition portion;
said transition portion outwardly projecting from said handle portion to said receptacle portion to connect said handle portion to said receptacle portion, said transition portion including an engagement section which engages said receptacle portion substantially adjacent to said compression region;
said transition portion including said engagement section not deforming substantially when said compression region is compressed so that a significant level of shear stress is imparted upon said sleeve assembly between said compression region of said receptacle portion and said engagement section of said transition portion when said compression region is compressed, the compression of said compression region causing said receptacle portion including said compression region to sever from said transition portion leaving said transition portion including said engagement section attached to said stick.

2. The sealed openable swap applicator of claim 1 wherein said engagement section is angled between 45° to 90° from said stick axis.

3. The sealed openable swap applicator of claim 1 wherein said handle portion and said receptacle portion of said sleeve assembly are substantially cylindrically shaped and said transition portion is substantially frustoconical shaped.

4. The sealed openable swap applicator of claim 3 wherein said engagement section is angled between 45° to 90° from said stick axis.

5. A sealed openable swap applicator comprising:
a swab;
an elongate small diameter stick attached to said swab, said stick defining a stick axis;
a thin walled sleeve assembly for encapsulating said swab and stick constructed of a relatively rigid plastic material that is manually compressible and severable at a desired region, said sleeve assembly including a handle portion, a receptacle portion and a transition portion therebetween;
said handle portion engaging said stick, and extending and encompassing a substantial part of the length of said stick;
said receptacle portion substantially enveloping said swab and being of a substantially greater cross section than said handle portion, said receptacle portion also including a compression region adjacent to said transition portion wherein compression of said compression region causes said receptacle portion to sever from said transition portion;

said transition portion outwardly projecting from said handle portion to said receptacle portion to connect said handle portion to said receptacle portion, said transition portion including an engagement section which engages said receptacle portion substantially adjacent to said compression region, said engagement section being angled between 45° to 90° from said stick axis;

said transition portion including said engagement section not deforming substantially when said compression region is compressed so that a significant level of shear stress is imparted upon said sleeve assembly between said compression region of said receptacle portion and said engagement section of said transition portion when said compression region is compressed, the compression of said compression region causing said receptacle portion including said compression region to sever from said transition portion leaving said transition portion including said engagement section attached to said stick.

6. The sealed openable swap applicator of claim 5 wherein said engagement section does not substantially deform inwardly when said compression region is compressed so that a significant level of shear stress is imparted upon said sleeve assembly between said compression region of said receptacle portion and said engagement section of said transition portion when said compression region is compressed.

7. The sealed openable swap applicator of claim 5 wherein said handle portion and said receptacle portion of said sleeve assembly are substantially cylindrically shaped and said transition portion is substantially fristoconically shaped.

8. The sealed openable swap applicator of claim 7 wherein said engagement section does not deform considerably inwardly when said compression region is compressed so that a significant level of shear stress is imparted upon said sleeve assembly between said compression region of said receptacle portion and said engagement section of said transition portion when said compression region is compressed.

* * * * *